United States Patent [19]

Hara et al.

[11] 4,254,195

[45] Mar. 3, 1981

[54] STABILIZATION OF ORGANIC SUBSTRATE MATERIALS INCLUDING PHOTOGRAPHIC DYE IMAGES AGAINST THE ACTION OF LIGHT

[75] Inventors: Hiroshi Hara, Asaka; Kotaro Nakamura; Yoshiaki Suzuki, both of Minami-ashigara, all of Japan

[73] Assignee: Fuji Photo Film Co., Ltd., Minami-ashigara, Japan

[21] Appl. No.: 29,086

[22] Filed: Apr. 11, 1979

[30] Foreign Application Priority Data

Apr. 14, 1978 [JP] Japan .................................. 53-43866

[51] Int. Cl.$^3$ ......................... G03C 1/40; G03C 1/84; G03C 7/00; G03C 1/10
[52] U.S. Cl. .......................................... 430/17; 8/636; 260/45.75 C; 260/45.75 M; 260/45.75 N; 260/45.75 R; 128/411; 128/500; 430/216; 430/372; 430/512; 430/517; 430/551; 430/559; 430/561
[58] Field of Search ................ 96/56, 77, 84 A, 84 R, 96/84 UV, 100, 99, 119 R; 8/4, 74; 423/366; 428/411, 500, 539; 260/45.75 C, 45.75 M, 45.75 N, 45.75 R; 430/17, 216, 372, 551, 559, 561, 512, 517

[56] References Cited

U.S. PATENT DOCUMENTS 2,615,860 10/1952 Burgess .......................... 260/45.75 C
4,050,938 9/1977 Smith et al. ........................ 96/84 A

OTHER PUBLICATIONS

Balch et al., "New Systems of Complexes . . . Reactions", *J. of Am. Chem. Soc.*, vol. 87, 5-20-65, pp. 2301, 2302.
Stiefel et al., "The Myth . . . Complexes", *J. of Am. Chem. Soc.*, vol. 87, 7-5-65, pp. 3016, 3017.
Balch et al., "Complete Electron Transfer . . . ", *J. Am. Chem. Soc.*, vol. 88, 11-20-66, pp. 5201-5209.
Holm et al., *J. Am. Chem. Soc.*, vol. 89, 6-7-67, pp. 2866-2874.

*Primary Examiner*—Richard L. Schilling

*Attorney, Agent, or Firm*—Sughrue, Rothwell, Mion, Zinn and Macpeak

[57] ABSTRACT

Organic substrate materials having absorption maxima between 300 and 800 nm can be stabilized against the action of light by the presence of at least one compound represented by either of the following general formula (I) or (II):

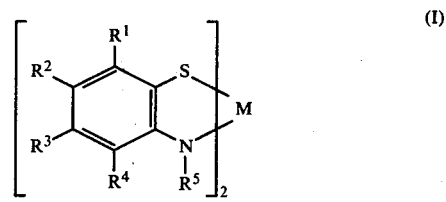

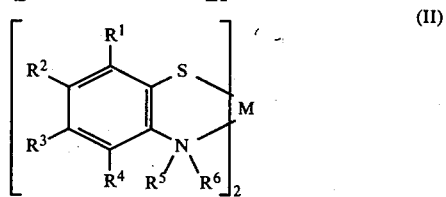

where M represents a metal atom selected from the group comprising Cu, Co, Ni, Pd and Pt; $R^1$, $R^2$, $R^3$ and $R^4$, may be the same or different and each represents a hydrogen atom, a halogen atom, cyano group, an alkyl group, an aryl group, a cycloalkyl group, or a heterocyclic ring, each of the latter four groups being bonded directly or via a divalent connecting group to the corresponding carbon atom of the benzene ring. Alternatively, $R^1$ and $R^2$, $R^2$ and $R^3$, or $R^3$ and $R^4$, may combine to represent the non-metallic atoms necessary to complete a 6-membered ring.

$R^5$ and $R^6$, may be the same or different and each represents a hydrogen atom, an alkyl group, an aryl group, an acyl group, an alkoxycarbonyl group, an aryloxycarbonyl group, an alkylsulfonyl group or an arylsulfonyl group.

14 Claims, No Drawings

STABILIZATION OF ORGANIC SUBSTRATE MATERIALS INCLUDING PHOTOGRAPHIC DYE IMAGES AGAINST THE ACTION OF LIGHT

BACKGROUND OF THE INVENTION

1. Field of the Invention

This invention relates to a method of stabilizing organic substrate materials against the action of light, and more particularly to a method of stabilizing organic dyestuffs to light irradiation.

2. Discussion of the Prior Art

Generally it is well known that many organic substrate materials such as, for example, organic dyestuffs tend to fade or discolor by the action of light. A number of studies on the prevention of such fading and/or discoloration of organic dyes, i.e., on the improvement of light-fastness have been carried out in the related technical fields including printing ink manufacture, textile dyeing and color photography. The instant invention provides a quite effective method for improving the light-fastness of dyes and other organic substrate materials.

In the present specification, the term "organic substrate material" or "substrate material" mean a substance which appears colored or colorless to the human eye under the irradiation of sunlight, inclusive of not only those substances having absorption peaks within the visible spectrum but also those with absorption peaks which lie in the U.V. and infrared regions. An exemplary compound of the latter type is an optical brightening agent. Hence, the organic substrate materials of the instant invention include organic compounds having absorption maxima between about 300 nm in the ultraviolet region and about 800 nm in the infrared region.

These organic substrate materials occur particularly in photographic materials, e.g., color films, prints, diffusion transfer units, etc., in colored polymers useful as a agricultural vinyl cover sheets, umbrellas, tents, etc.; fluorescent whitening agents; and dyed textiles, etc., and this invention is directed to improving the light fastness of these materials in each of these fields.

The term "dye" or "dyestuff" as used in the instant specification means an organic substance which appears colored to the human eye under the irradiation of sunlight.

Further, the term "light" refers to all forms of actinic radiation having wavelengths below about 800 nm, thus including ultraviolet light up to about 400 nm, visible light between about 400 and about 700 nm and infrared light of from about 700 to about 800 nm in wavelength.

With regard to the well-known tendency of organic substrate materials to undergo dye fading or discoloration under the influence of actinic radiation, various methods of improving light-fastness have been proposed. Such methods are exemplified by the one set forth in U.S. Pat. No. 3,432,300 wherein phenol-type compounds having a fused heterocyclic ring structure together are used with substrate materials such as indophenol, indoaniline, azo and azomethine-type dyes to improve the fastness of these dyes to the action of visible and UV light.

In the art of silver halide photographic light-sensitive materials, the oxidation product of an aromatic primary amine developing agent reacts with a coupler to form an azomethine- or indoaniline-type dye, as is described in Chapter 17 of "The Theory of the Photographic Process" authored by C. E. K. Mees and T. H. James (Macmillan Co., 1967). A number of methods for enhancing the stability to light of these photographic dye images have been proposed, including those set forth in U.S. Pat. Nos. 2,360,295, 2,418,613, 2,675,314, 2,701,197, 2,704,713, 2,728,659, 2,732,300, 2,735,765, 2,710,801 and 2,816,028, British Pat. No. 1,363,921, etc., all based on the use of hydroquinone derivatives; those set forth in U.S. Pat. Nos. 3,457,079 and 3,069,262, Japanese Patent Publication No. 13,496/1968, etc., all using gallic acid derivatives; those set forth in U.S. Pat. Nos. 2,735,765 and 3,698,909 using p-alkoxyphenols; those set forth in U.S. Pat. Nos. 3,432,300, 3,573,050, 3,574,627, 3,764,337, 3,574,626, 3,698,909 and 4,015,990, using chroman and coumarane derivatives, etc. However, these customarily known compounds do not exhibit a sufficient degree of fade or discoloration prevention ability.

British Pat. No. 1,451,000 discloses a method for stabilizing organic substrate materials against the action of light using azomethine quenching compounds which have absorption peaks at longer wavelengths than the substrate materials. This method has a serious drawback that the deep color of the azomethine quencher itself deteriorates the color hue of the substrate material.

The use of metal chelate compounds for the purpose of preventing the light-induced degradation of polymers is described in the following papers; J. P. Guillory & R. S. Becker, *J. Polym. Sci.*, Polym. Chem. Ed. 12, pp. 993 (1974), and R. P. R. Ranaweera & G. Scott, *J. Polym. Sci.*, Polym. Lett. Ed., 13, pp. 71 (1975). Metal chelate compounds are also used for the stabilization of dyestuffs as is disclosed in Japanese Patent Application (OPI) No. 87,649/1975 and Research Disclosure No. 15162 (1976). However, the chelate compounds disclosed in the above literature are not only effective to an unsatisfactory degree, but are provided with too low solubilities in many organic solvents to permit their incorporation into the system at a concentration level high enough to exert the effect of fade prevention. Moreover, most of these chelates are so deeply colored themselves that their presence at higher concentration levels adversely affects the color hue and the color purity of the substrate material (particularly dyestuffs) involved.

SUMMARY OF THE INVENTION

Accordingly, one object of the instant invention is to provide a method of stabilizing organic substrate materials against the action of light.

Another object of the instant invention is to provide a method of stabilizing organic substrate materials, such as, in particular, an organic dyestuff against the action of light without deteriorating its color hue and purity.

Still another object of the instant invention is to provide a method of stabilizing organic substrate materials against the action of light using a stabilizing agent having a high degree of affinity for the organic substrate material as well as sufficient solubility in common organic solvents.

A further object of the instant invention is to provide a stabilizing method suited for dye images provided by color photography.

Still another object of the instant invention is to provide a method of stabilizing dyestuffs which can be formed by the reaction between an aromatic primary amine developing agent and a color coupler against the action of light.

Still another object of this invention is to improve the light fastness of colored polymers useful as agricultural vinyl sheets, umbrellas, tents, etc.

Still other objects of the instant invention will become more clear from the following description of the invention.

DETAILED DESCRIPTION OF THE INVENTION

These and other objects of the instant invention have been achieved by making at least one compound represented by one of the following formulae (I) and (II) coexist with an organic substrate material having an absorption peak between about 300 nm and about 800 nm.

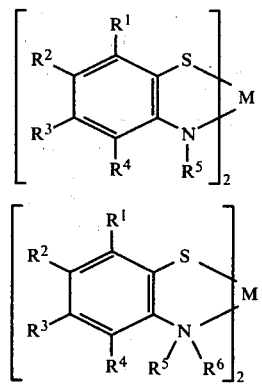

The terms "in the presence of" or "coexistant with" as used in the specification refer not only to the coexistence of the substrate material and the compound of the formulae (I) and (II) in the same solution, dispersion, emulsion or layer, but also to the existence of the organic substrate material and the complex in, for example, adjacent layers of a multi-layer photographic material. As long as the complex compound is associated with the organic substrate material such that it improves the light fastness of the organic substrate, it is used "in the presence of" or it "coexists with" the substrate for purposes of the present invention.

In the above formulae, M represents a metal atom selected from Cu, Co, Ni, Pd and Pt.

$R^1$, $R^2$, $R^3$ and $R^4$ may be the same or different and each represents a hydrogen atom, a halogen atom, a cyano group, an alkyl group, an aryl group, a cycloalkyl group, or a heterocyclic group which is bonded to the carbon atom in the benzene ring directly or in the case of the latter four members via a divalent connecting group. Alternatively, $R^1$ and $R^2$, $R^2$ and $R^3$, and $R^3$ and $R^4$ each represents a non-metallic atomic group necessary to complete a 6-membered ring.

The halogen atoms for $R^1$, $R^2$, $R^3$ or $R^4$ include fluorine, chlorine, bromine and iodine atoms.

The alkyl group represented by $R^1$, $R^2$, $R^3$ or $R^4$ include preferably those with from 1 to 19 carbon atoms, which may be straight-chained or branched, and which may be substituted or unsubstituted (e.g., methyl, ethyl, propyl, butyl, hexyl, octyl, decyl, dodecyl, tetradecyl, hexadecyl, octadecyl, etc.).

The aryl group for $R^1$, $R^2$, $R^3$ or $R^4$ contain preferably from 6 to 14 carbon atoms, and may be substituted or unsubstituted (e.g., phenyl, and naphthyl).

The heterocyclic group represented by $R^1$, $R^2$, $R^3$ or $R^4$ is preferably a 5- or 6-membered ring, which may be substituted or unsubstituted, containing in the ring at least one hetero atom selected from nitrogen, oxygen and sulfur (e.g., furyl, hydrofuryl, thienyl, pyrrolyl, pyrrolydyl, pyridyl, imidazolyl, pyrazolyl, quinolyl, indolyl, oxazolyl, thiazolyl, etc.).

The cycloalkyl group represented by $R^1$, $R^2$, $R^3$ or $R^4$ is preferably a 5- or 6-membered ring, which may be substituted or unsubstituted (e.g., cyclopentyl, cyclohexyl, etc.).

The 6-membered ring formed by combining $R^1$ with $R^2$, $R^3$ with $R^4$, or $R^2$ with $R^3$ is preferably a benzene ring, which may be substituted or unsubstituted, and further be a part of a fused structure (e.g., benzene, naphthalene, isobenzothiophene, isobenzofuran, isoindoline rings, etc.).

All of the above-cited alkyl, cycloalkyl, aryl and heterocyclic groups represented by $R^1$, $R^2$, $R^3$ or $R^4$ can be bonded to the carbon atoms in the benzene ring in the general formulae via a divalent connecting group such as, an oxy (—O—) group, a thio (—S—) group, an amino group, an oxycarbonyl group, a carbonyl group, a carbamoyl group, a sulfamoyl group, a carbonylamino group, a sulfonyl group, a carbonyloxy group, a sulfonylamino group, etc.

Examples of the alkyl group represented by $R^1$, $R^2$, $R^3$ or $R^4$ bonded to the carbon atom in the benzene ring through one of the above-cited divalent connecting groups include a $C_1$–$C_{20}$ alkoxy group (e.g., methoxy, ethoxy, propoxy, butoxy, n-decyloxy, n-dodecyloxy, n-hexadecyloxy, etc.), an alkoxycarbonyl group having 1 to 20 carbon atoms in the alkyl moiety (e.g., methoxycarbonyl, ethoxycarbonyl, butoxycarbonyl, n-decyloxycarbonyl, n-hexadecyloxycarbonyl, etc.), a $C_2$–$C_{20}$ acyl group (e.g., acetyl, valeryl, stearoyl, benzoyl, toluoyl, etc.), a $C_2$–$C_{20}$ acyloxy group (e.g., acetoxy, hexadecylcarbonyloxy, etc.), a $C_1$–$C_{20}$ alkylamino group (e.g., n-butylamino, N,N-diethylamino, N,N-didecylamino, etc.), an alkylcarbamoyl group having 1 to 20 carbon atoms in the alkyl moiety (e.g., butylcarbamoyl, N,N-diethylcarbamoyl, n-dodecylcarbamoyl, etc.), an alkylsulfamoyl group having 1 to 20 carbon atoms in the alkyl moiety (e.g., butylsulfamoyl, N,N-diethylsulfamoyl, n-dodecylsulfamoyl, etc.), an sulfonylamino group including an alkyl sulfonylamino group having 1 to 20 carbon atoms in the alkyl moiety (e.g., methylsulfonylamino, butylsulfonylamino, etc.), an alkylsulfonyl group having 1 to 20 carbon atoms in the alkyl moiety (e.g., mesyl, ethanesulfonyl, etc.), a $C_2$–$C_{20}$ acylamino group (e.g., acetylamino, valerylamino, parmitoylamino, benzoylamino, toluoylamino, etc.), etc.

Examples of the cycloalkyl group represented by $R^1$, $R^2$, $R^3$ and $R^4$ bonded to the carbon atom in the ring structure via a divalent connecting group include a cyclohexyloxy group, a cyclohexylcarbonyl group, a cyclohexyloxycarbonyl group, a cyclohexylamino group, etc.

Examples of the aryl group represented by $R^1$, $R^2$, $R^3$ or $R^4$ bonded to the carbon atom in the benzene ring structure of the compound characterizing the instant invention via one of the divalent connecting groups include a $C_6$–$C_{14}$ aryloxy group (e.g., phenoxy, naphthoxy, etc.), an aryloxycarbonyl group having 6 to 14 carbon atoms in the aryl moiety (e.g., phenoxycarbonyl, naphthoxycarbonyl, etc.), an acyl group (e.g., benzoyl, naphthoyl, etc.), an anilino group (e.g., phenylamino, N-methylanilino, N-acetylanilino, etc.), a $C_6$–$C_{14}$ acyloxy group (e.g., benzoyloxy, toluoyloxy, etc.), an arylcarbamoyl group having 6 to 14 carbon atoms in the aryl moiety (e.g., phenylcarbamoyl, etc.), an arylsulfamoyl group having 6 to 14 carbon atoms in the aryl moiety (e.g., phenylsulfamoyl, etc.), an arylsulfonylamino group having 6 to 14 carbon atoms in the aryl moiety (phenylsulfonylamino, p-tolissulfonylamino, etc.), an arylsulfonyl group having 6 to 14 carbon atoms in the aryl moiety (e.g., benzensulfonyl, tosyl, etc.), a $C_6$–$C_{14}$ acylamino group (e.g., benzoylamino, etc.), etc.

The 6-membered ring group formed by coupling $R^1$ with $R^2$, $R^2$ with $R^3$, or $R^3$ with $R^4$, and the alkyl, aryl, heterocyclic and cycloalkyl groups represented by $R^1$, $R^2$, $R^3$ and $R^4$ and exemplified above may be substituted by the following substituents; a halogen atom (e.g., chlorine, bromine, fluorine, etc.), a cyano group, a straight-chained or branched $C_1$–$C_{20}$ alkyl group (e.g., methyl, ethyl, propyl, butyl, hexyl, octyl, decyl, dodecyl, tetradecyl, hexadecyl, heptadecyl, octadecyl, methoxyethoxyethyl, etc.), a $C_6$–$C_{14}$ aryl group (e.g., phenyl, tolyl, naphthyl, chlorophenyl, methoxyphenyl, acetylphenyl, etc.), a $C_1$–$C_{20}$ alkoxy group (e.g., methoxy, ethoxy, butoxy, propoxy, methoxyethoxy, etc.), a $C_6$–$C_{14}$ aryloxy group (e.g., phenoxy, tolyloxy, naphthoxy, methoxyphenoxy, etc.), an alkoxycarbonyl group (e.g., methoxycarbonyl, butoxycarbonyl, phenoxymethoxycarbonyl, etc.), an aryloxycarbonyl group having 6 to 14 carbon atoms in the aryl moiety (e.g., phenoxycarbonyl, tolyloxycarbonyl, methoxyphenoxycarbonyl, etc.), a $C_2$–$C_{20}$ acyl group (e.g., formyl, acetyl, valeryl, stearoyl, benzoyl, toluoyl, naphthoyl, p-methoxybenzoyl, etc.), a $C_2$–$C_{20}$ acyloxy group (e.g., acetoxy, hexadecylcarbonyloxy, etc.), a $C_2$–$C_{20}$ acylamino group (e.g., acetamide, benzamide, methoxyacetamide, etc.), an anilino group (e.g., phenylamino, N-methylanilino, N-phenylanilino, N-acetylanilino, etc.), a $C_1$–$C_{20}$ alkylamino group (e.g., n-butylamino, N,N-diethylamino, 4-methoxy-n-butylamino, etc.), a carbamoyl group including an alkylcarbamoyl group having 1 to 20 carbon atoms in the alkyl moiety (e.g., n-butylcarbamoyl, N,N-diethylcarbamoyl, etc.), a sulfamoyl group including a $C_1$–$C_{20}$ alkylsulfamoyl group (e.g., n-butylsulfamoyl, N,N-diethylsulfamoyl, n-dodecylsulfamoyl, N-(4-methoxy-n-butyl)sulfamoyl, etc.), a sulfonylamino group including a $C_1$–$C_{20}$ alkylsulfonylamino group (e.g., methylsulfonylamino, methoxymethylsulfonylamino, etc.) and a $C_6$–$C_{14}$ arylsulfonylamino group (e.g., phenylsulfonylamino, etc.), a sulfonyl group including a $C_1$–$C_{20}$ alkyl sulfonyl group (e.g., mesyl, tosyl, methoxymethanesulfonyl, etc.), etc.

The alkyl group represented by $R^5$ or $R^6$ includes substituted and unsubstituted straight and branched-chained alkyl groups. The alkyl groups should preferably have from 1 to 20 carbon atoms excluding the carbon atoms in any substituents (e.g., methyl, ethyl, propyl, butyl, hexyl, octyl, decyl, dodecyl, tetradecyl, hexadecyl, heptadecyl, octadecyl, etc.).

The aryl group represented by $R^5$ or $R^6$ includes both substituted and unsubstituted mono- and bi cyclic aryl groups having preferably from 6 to 14 carbons atoms excluding the carbon atoms in any substituents. Examples are phenyl, tolyl, naphthyl, etc.

The acyl group represented by $R^5$ or $R^6$ may be substituted or unsubstituted and preferably contains from 2 to 21 carbon atoms excluding the carbon atoms in any substituents, and is exemplified by acetyl, valeryl, stearoyl, benzoyl, naphthoyl, etc.

The alkoxycarbonyl group represented by $R^5$ or $R^6$ may be substituted or unsubstituted and preferably contains from 2 to 21 carbon atoms excluding the carbon atoms in any substituents, and is exemplified by methoxycarbonyl, butyoxycarbonyl, propoxycarbonyl, etc.

The aryloxycarbonyl group represented by $R^5$ or $R^6$ includes both substituted and unsubstituted groups and preferably contains from 7 to 15 carbon atoms excluding the carbon atoms in any substituents. Exemplary groups are phenoxycarbonyl, tolyloxycarbonyl, etc.

The alkylsulfonyl group represented by $R^5$ or $R^6$ includes substituted and unsubstituted groups containing desirably from 1 to 20 carbon atoms excluding the carbon atoms in any substituents. Examples are mesyl, butanesulfonyl, etc.

The arylsulfonyl group represented by $R^5$ or $R^6$ includes both substituted and unsubstituted groups preferably containing from 6 to 14 carbon atoms excluding the carbon atoms in any substituents. Exemplary are benzenesulfonyl, tosyl, etc.

Of the chelate compounds represented by general formula (I) and (II), those specifically suited for the instant invention can be expressed by the following general formulae (Ia) and (IIa).

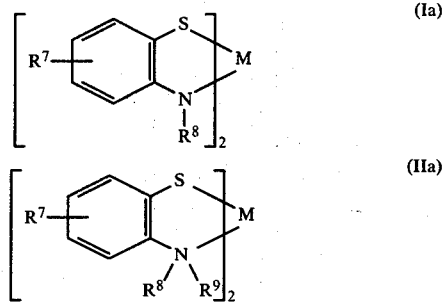

In the formulae, M represents the same metal atoms as defined in formulae (I) and (II).

$R^7$ has the same definition as the substituents defined by $R^1$, $R^2$, $R^3$ and $R^4$ in formulae (I) and (II).

$R^8$ and $R^9$ each represents the same groups defined by $R^5$ and $R^6$ in the formulae (I) and (II).

The following compounds which fall within formulae (I) and (II) are cited for the purpose of exemplifying particularly effective chelate compounds for the instant invention, but they are not to be construed as limiting the scope of the invention.

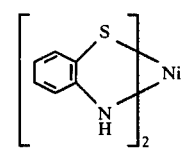

1-1

-continued

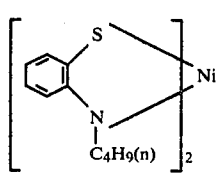 1-2

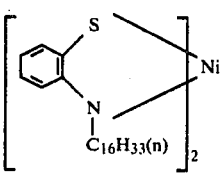 1-3

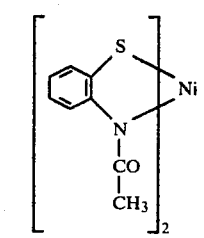 1-4

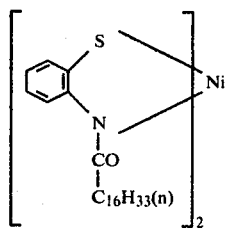 1-5

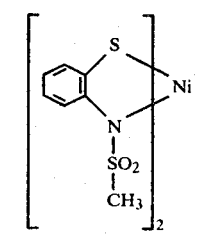 1-6

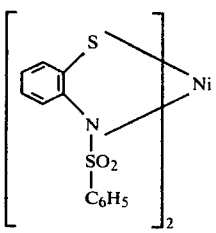 1-7

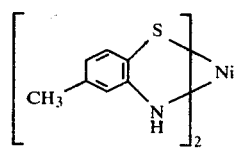 1-8

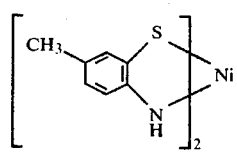 1-9

-continued

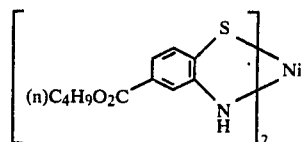 1-10

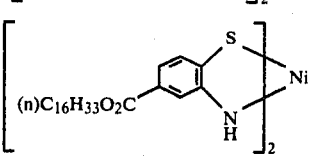 1-11

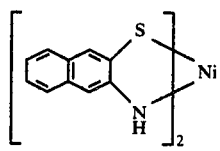 1-12

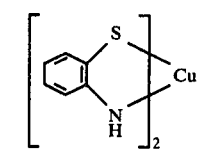 1-13

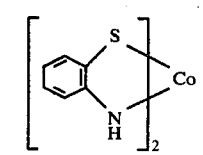 1-14

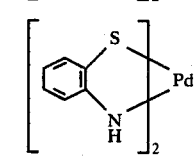 1-15

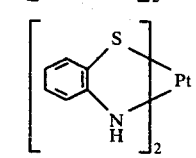 1-16

For the general synthetic procedures for these illustrated chelate compounds, reference can be made to the following reports:

A. L. Balch, F. Röhrscheid, & R. H. Holm; *J.A.C.S.*, pp. 2301 (1965)

A. L. Balch & R. H. Holm; *J.A.C.S.*, 88, pp. 5201 (1966)

E. I. Stiefel, J. H. Waters, E. Billig & H. B. Gray; *J.A.C.S.*, 87, pp. 3016 (1965)

R. H. HOLM, A. L. Balch, A. Dairson, A. H. Maki & T. E. Berry; *J.A.C.S.*, 89, pp. 2866 (1967)

A solution of 2-aminobenzenethiol derivatives in a solvent mixture of a lower alcohol and water is added to a mixture of a metal salt such as nickel chloride or cobalt chloride and concentrated ammonia water. The precipitate formed is dispersed in an aqueous potassium hydroxide solution. Air is blown into the dispersion. The precipitate thus formed is purified in a conventional manner.

SYNTHESIS EXAMPLE 1

Synthesis of Compound I-1

Into an ethanol-water mixture comprising 160 ml ethanol and 40 ml water were dissolved 10.0 g o-aminothiophenol and 4.4 g potassium hydroxide. The resulting solution was added to another solution prepared by dissolving 9.4 g nickel chloride hexahydrate and 30 ml concentrated ammonia water in 150 ml water. The precipitate formed was separated by filtration, rinsed first with water and then with ethanol. Finally, the precipitate was dried under reduced pressure. The thus prepared chelate compound, Ni bis(o-aminothiophenolate) was dispersed in 600 ml water containing 8 g potassium hydroxide, an air stream was passed through the dispersion for 8 hours whereby a deep blue precipitate deposited. By rinsing the precipitate separated by filtration with water, drying under reduced pressure, and subjecting the dried product to ether extraction with a Soxlet extractor, 9 g of a blue crystalline product was obtained.

SYNTHESIS EXAMPLE 2

Synthesis of Compound I-10

22 g of 4-(n-buthoxycarbonyl)-2-aminobenzenethiol was dissolved in a mixture of 200 ml ethanol and 50 ml water together with 5.6 g potassium hydroxide. The resulting solution was added to another solution prepared by dissolving 12.0 g nickel chloride hexahydrate and 38 ml concentrated ammonium aqueous solution in 200 ml water. Precipitation took place and the precipitate was collected by filtration, washed first with water and then with a small quantity of cold ethanol and dried under reduced pressure. The thus prepared bis(o-aminothiophenolate) type chelate compound was dispersed in 700 ml water containing 10.2 g potassium hydroxide. Air was passed through the dispersion for 8 hours whereby a deep blue product precipitated. By collecting the precipitate by filtration, washing with water, drying under reduced pressure and recrystallizing from a methylene chloride/hexane mixture, one obtained a purified, deep blue crystalline product of 8 g.

As will be apparent from the extensive discussion and examples of the organic substrate which follows, the present invention is effective with a very wide variety of organic materials, the essential point being that the substrate materials have a maximum absorption wavelength in the range of 300 to 800 nm.

The organic substrate materials in this invention include all dyes belonging to the following classes based on dyeing property, i.e., water-soluble dyes such as basic dyes, acid dyes, direct dyes, soluble vat dyes, mordant dyes, etc.; water-insoluble dyes such as sulfur dyes, vat dyes, oil colors, disperse dyes, azoic dyes, acid dyes, etc.; and reactive dyes. These organic substrate materials include not only the dyes which are seen as colored materials under sunlight but also colorless or light yellow optical whitening agents.

Of these dyes, the dyes preferably used in conjunction with this invention are quinoneimine dyes (e.g., azine dyes, oxazine dyes, thiazine dyes, etc.), methine and polymethine dyes (e.g., cyanine dyes, azomethine dyes, etc.), azo dyes, anthraquinone dyes, indoamine dyes, indophenol dyes, indigoid dyes, carbonium dyes, formazan dyes, etc., classified by chemical structure.

The organic substrate materials in this invention also include image-forming dyes used in the field of photography, for example, the dyes formed from color couplers, DRR compounds, DDR couplers, amidrazone compounds, dye developers, etc., and dyes for the silver dye bleach process.

Preferred organic substrate materials in this invention are anthraquinone dyes, quinoneimine dyes, azo dyes, methine dyes, polymethine dyes, indoamine dyes, indophenol dyes, and formazan dyes.

Furthermore, examples of the most preferred dyes used at the practice of this invention are methine dyes, polymethine dyes, indoamine dyes and indophenol dyes. The methine dyes, polymethine dyes, indoamine dyes, and indophenol dyes also include compounds having the following moiety

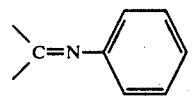

wherein the phenyl group may be substituted by an alkyl group, an alkoxy group, a halogen atom, or an amino group.

The dye-forming couplers suitably used in this invention include yellow dye-forming couplers, magenta dye-forming couplers and cyan dye-forming couplers. These couplers may be so-called 4-equivalent couplers or 2-equivalent couplers as described in U.S. Pat. Nos. 3,277,155 and 3,458,315.

The yellow dye-forming couplers generally contain at least one methylene group activated by a carbonyl group (for example, open chain type ketomethylene groups) and include $\beta$-diketones and $\beta$-ketoacylamides such as, for example, benzylacetanilide and $\alpha$-pivalylacetanilide. Examples of the suitable yellow couplers used in this invention are described in U.S. Pat. Nos. 2,428,054, 4,026,706, 2,499,966, 2,453,661, 2,778,658, 2,908,573, 3,227,550, 3,253,924, 3,277,155 and 3,384,657 and British Pat. No. 503,752.

As the magenta dye-forming couplers used in this invention, there are, for example, 5-pyrazolone type couplers. The couplers of this type are described in, for example, U.S. Pat. Nos. 2,600,788, 2,725,292, 2,908,573, 3,006,759, 3,062,653, 3,152,896, 3,227,550, 3,252,924, 4,026,706 and 3,311,476.

Other magenta dye-forming couplers used in this invention are the indazolones of the type as described in Vittum and Weissberger, *Journal of Photographic Science*, Vol. 6, page 158 et seq. (1958) and practical examples of such magenta dye-forming couplers are pyrazolinobenzimidazoles as described in U.S. Pat. No. 3,061,432, pyrazolo-s-triazoles as described in Belgian Patent No. 724,427, and 2-cyanoacetylcumarones as described in U.S. Pat. No. 2,115,394.

The cyan dye-forming couplers which can be used in this invention include phenol compounds and $\alpha$-naphthol compounds. The compounds of this type are illustrated in U.S. Pat. Nos. 2,275,292, 2,423,730, 2,474,293, 2,895,826, 2,908,573, 3,043,892, 4,026,706, 3,227,550 and 3,253,294.

In general, the couplers described above are further described in, for example, Kirk-Othmer, *Encyclopedia of Chemical Technology*, Vol. 5, pages 822–825 and Glafkides, *Photographic Chemistry*, Vol. 2, pages 596–614.

As described above, when such couplers are used in the practice of this invention, dyes are formed by the reaction of these couplers and an oxidized aromatic primary amine silver halide developing agent.

The developing agent described above includes an aminophenol and a phenylenediamine and they may include a mixture of them.

Typical examples of the developing agent which can form the organic substrate materials by combining various couplers are illustrated as follows:

A 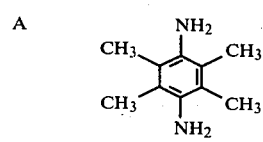
B 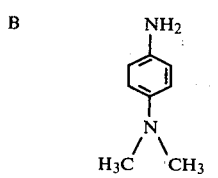
C 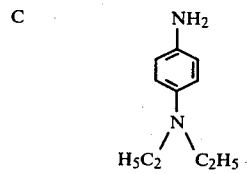
D 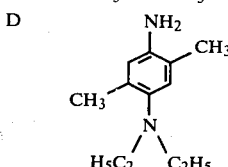
E 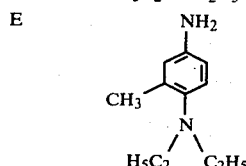
F 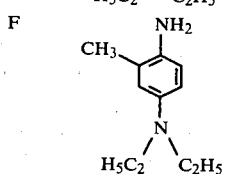
G 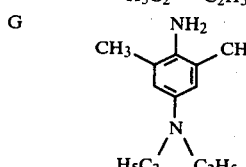
H 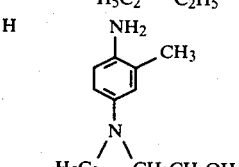
I 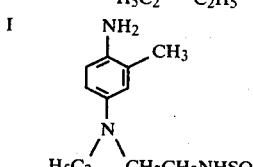
J 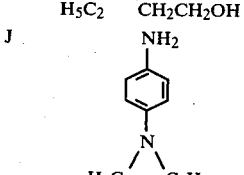
K 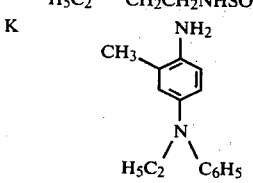
L 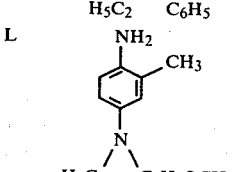

One representative class of the developing agent capable of forming organic substrate materials of the instant invention by reaction with a variety of couplers consists of p-phenylene diamine and its derivatives which are set forth in *The Theory of the Photographic Process*, 4th Edition, edited by T. H. James and published by Macmillan Co. (1977) from pp 315 to 320. p-Phenylene diamine derivatives in which at least one amino group thereof is substituted by a lower alkyl group with from 1 to 3 carbon atoms are specifically suited to practice the instant invention. Exemplary compounds include 4-amino-N,N-dimethylaniline, 4-amino-N,N-diethylaniline, 4-amino-3-methyl-N,N-diethylaniline, 4-amino-3-methyl-N-ethyl-N-(β-methanesulfonamide-ethyl)aniline, 4-amino-N-ethyl-N-(β-hydroxyethyl)aniline, 4-amino-3-methyl-N-ethyl-N-(β-hydroxyethyl)aniline, etc.

Cyan, magenta and yellow couplers which are preferably employed are represented by the formulae (III), (IV) and (V) below, respectively:

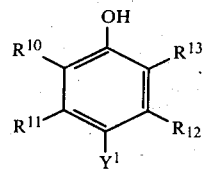

(III)

wherein $R^{10}$, $R^{11}$, $R^{12}$ and $R^{13}$ each represents a hydrogen atom, a halogen atom (e.g., fluorine, chlorine, bromine or iodine), an alkyl group having 1 to 20 carbon atoms (e.g., methyl, ethyl, octyl, dodecyl, tetradecyl, octadecyl, etc.); an alkyl- or aryl-substituted carbamoyl group wherein the aryl moiety has 6 to 10 carbon atoms (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R^{10}$ and $R^{11}$ may combine with each other to form a 6-membered carbocyclic ring (e.g., a benzene ring which may further be substituted with a $C_1$-$C_{20}$ alkyl or $C_6$-$C_{14}$ aryl group).

$Y^1$ represents a hydrogen atom, a halogen atom (e.g., fluorine, chlorine, bromine or iodine); or a group which is releasable upon reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an aminosulfonyloxy group, an alkylcarbonyloxy group, an arylcarbonyloxy group, an alkylthio group, an arylthio group, a heterocyclic ring thio group, etc., the details of which are well known in the art.

The alkyl, carbamoyl, sulfamoyl and amido groups expressed by $R^{10}$, $R^{11}$, $R^{12}$ and $R^{13}$, or the 6-membered ring formed by combining $R^{10}$ and $R^{11}$ with each other can also be substituted with other substituents, for example, a $C_1$-$C_{20}$ alkyl group (e.g., methyl, ethyl, propyl, octyl, dodecyl, tetradecyl, octadecyl, etc.); a $C_6$-$C_{14}$ aryl group (e.g., phenyl, tolyl, naphthyl, etc.); a $C_6$-$C_{14}$ aryloxy group (e.g., phenoxy, 2,5-di(t)-amylphenoxy, etc.); a halogen atom (e.g., chlorine, bromine, fluorine, etc.); and the like.

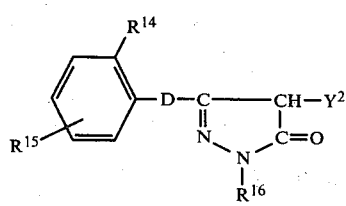

(IV)

wherein $R^{14}$ represents a hydrogen atom, a halogen atom (e.g., chlorine, bromine, fluorine, etc.); a $C_1$-$C_{20}$ alkyl group (e.g., methyl, ethyl, n-propyl, etc.); or a $C_1$-$C_{20}$ alkoxy group (e.g., methoxy, ethoxy, etc.); $R^{15}$ represents a $C_1$-$C_{20}$ alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group wherein the alkyl moiety contains 1 to 20 carbon atoms (e.g., decylcarbamoyl, tetradecylcarbamoyl, octadecylcarbamoyl, etc.); an N-alkylsulfamoyl group wherein the alkyl moiety contains 1 to 20 carbon atoms (e.g., decylsulfamoyl, tetradecylsulfamoyl, octadecylsulfamoyl, etc.); an alkoxycarbonyl group wherein the alkyl moiety contains 1 to 20 carbon atoms (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc., and $R^{16}$ represents a $C_6$-$C_{14}$ aryl group (e.g., phenyl, naphthyl, etc.), said alkyl and aryl groups having 1 to 20 and 6 to 14 carbon atoms respectively.

D represents an amino group, a carbonylamino group, or a ureido group.

$Y^2$ represents a hydrogen atom, a halogen atom (e.g., chlorine, bromine, etc.); or a group which is releasable upon reaction with the oxidation product with a developing agent (e.g., an arylazo group, an aryloxy group, an acyloxy group, an alkylthio group, an arylthio group, etc.). Such groups are well known.

The alkyl or alkoxy group represented by $R^{14}$, the alkyl, amido, N-alkylcarbamoyl, N-alkylsulfamoyl, alkoxycarbonyl or acyloxy group represented by $R^{15}$, or the aryl group represented by $R^{16}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

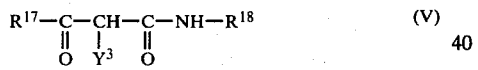
(V)

wherein $R^{17}$ represents a $C_1$-$C_{20}$ alkyl group (e.g., methyl, ethyl, (t)-butyl, (t)-octyl, etc.) or a $C_6$-$C_{14}$ aryl group (e.g., phenyl) and $R^{18}$ represents a $C_6$-$C_{14}$ aryl group (e.g., phenyl).

$Y^3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R^{17}$ and the aryl group represented by $R^{18}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc. the alkyl and aryl moieties of which contain 1 to 20 and 6 to 14 carbon atoms respectively.

In the following, couplers which can provide the organic substrate material of the instant invention particularly in the form of a photographic dye are listed for the purpose of illustration.

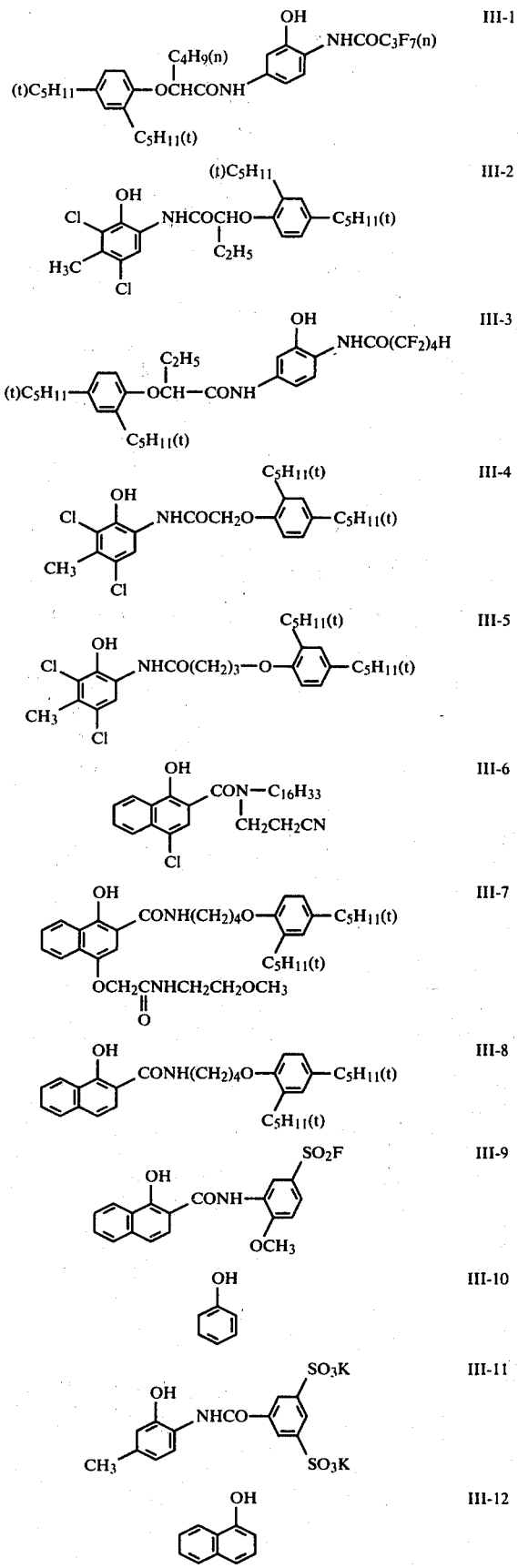

-continued
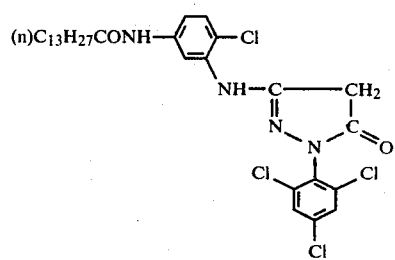
IV-1
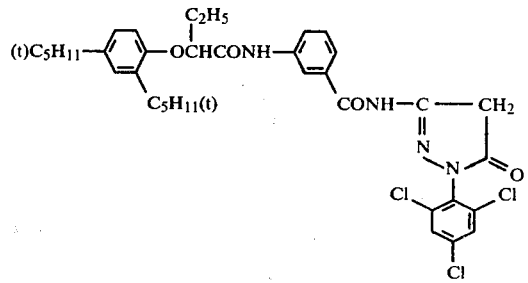
IV-2
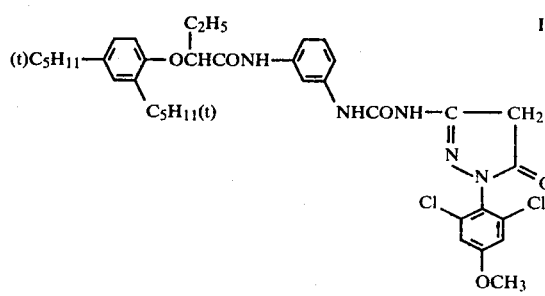
IV-3
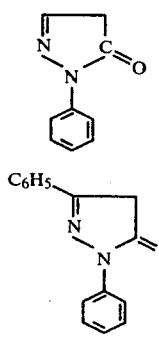
IV-4
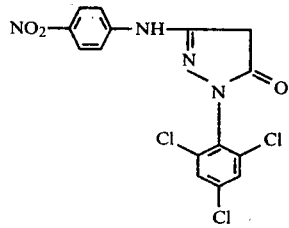
IV-5
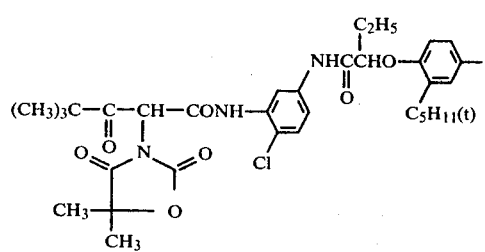
IV-6
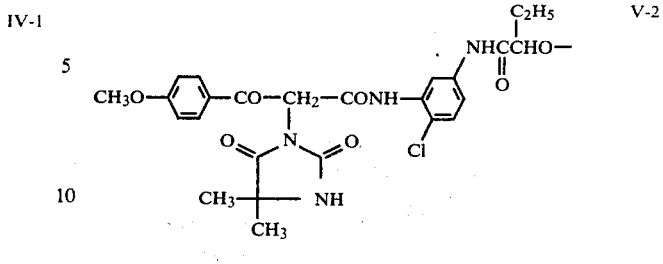
V-1
-continued
V-2
The following structural formulae exemplify dyestuffs or dye precursors which can be used for the instant invention as substrate materials.
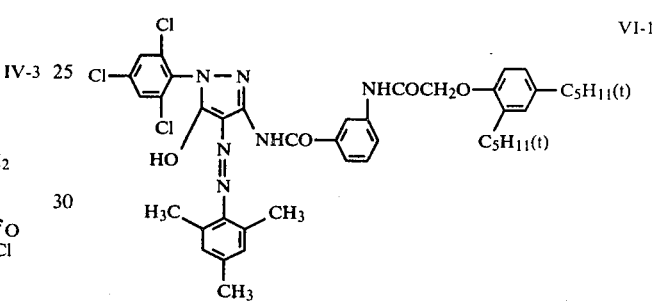
VI-1
VI-2
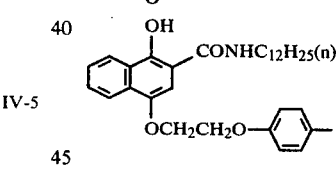
VI-3
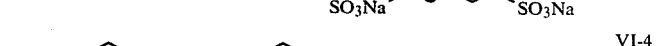
VI-4
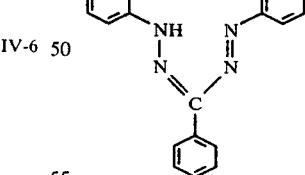
VI-5
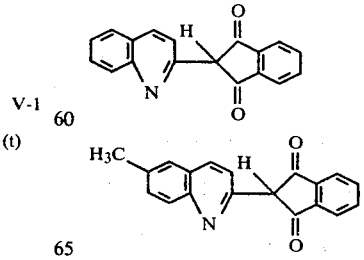
VI-6

-continued
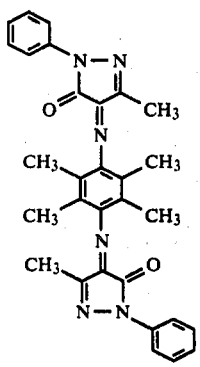 VI-7
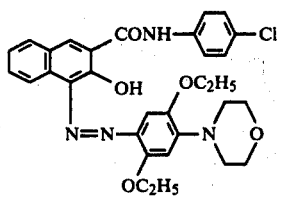 VI-8
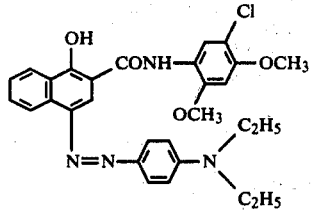 VI-9
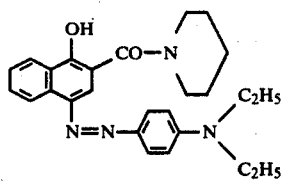 VI-10
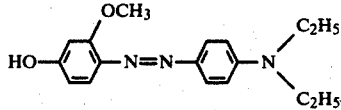 VI-11
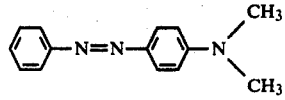 VI-12
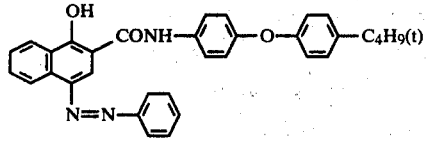 VI-13
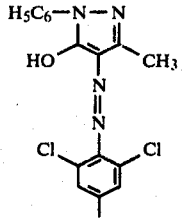 VI-14
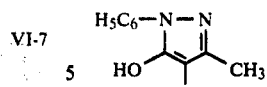 VI-15
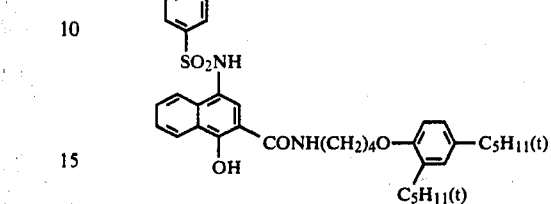 VI-16
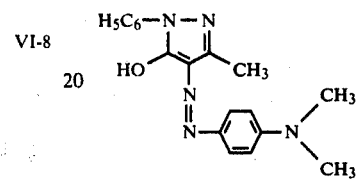 VI-17
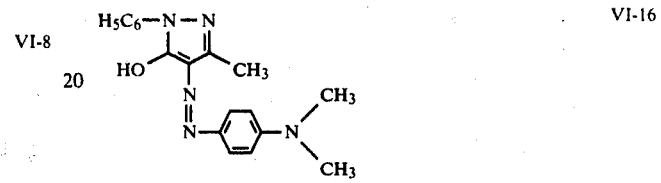 VI-18
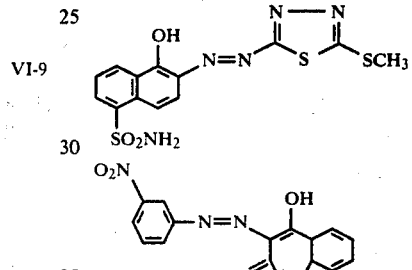 VI-19
 VI-20
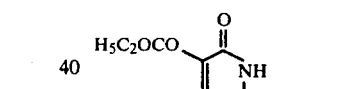 VI-21
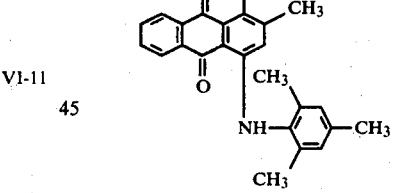 VI-22

-continued
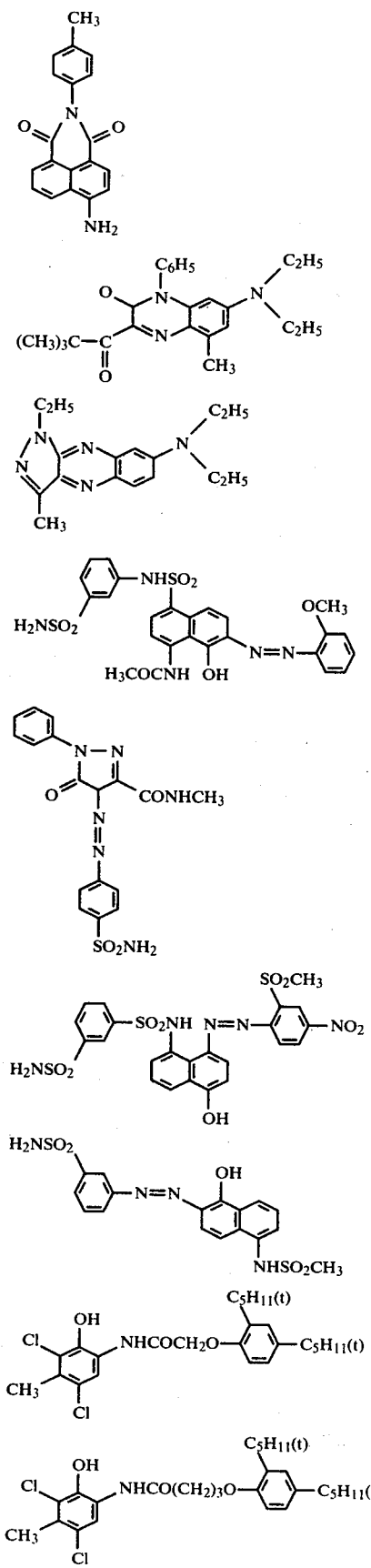
-continued
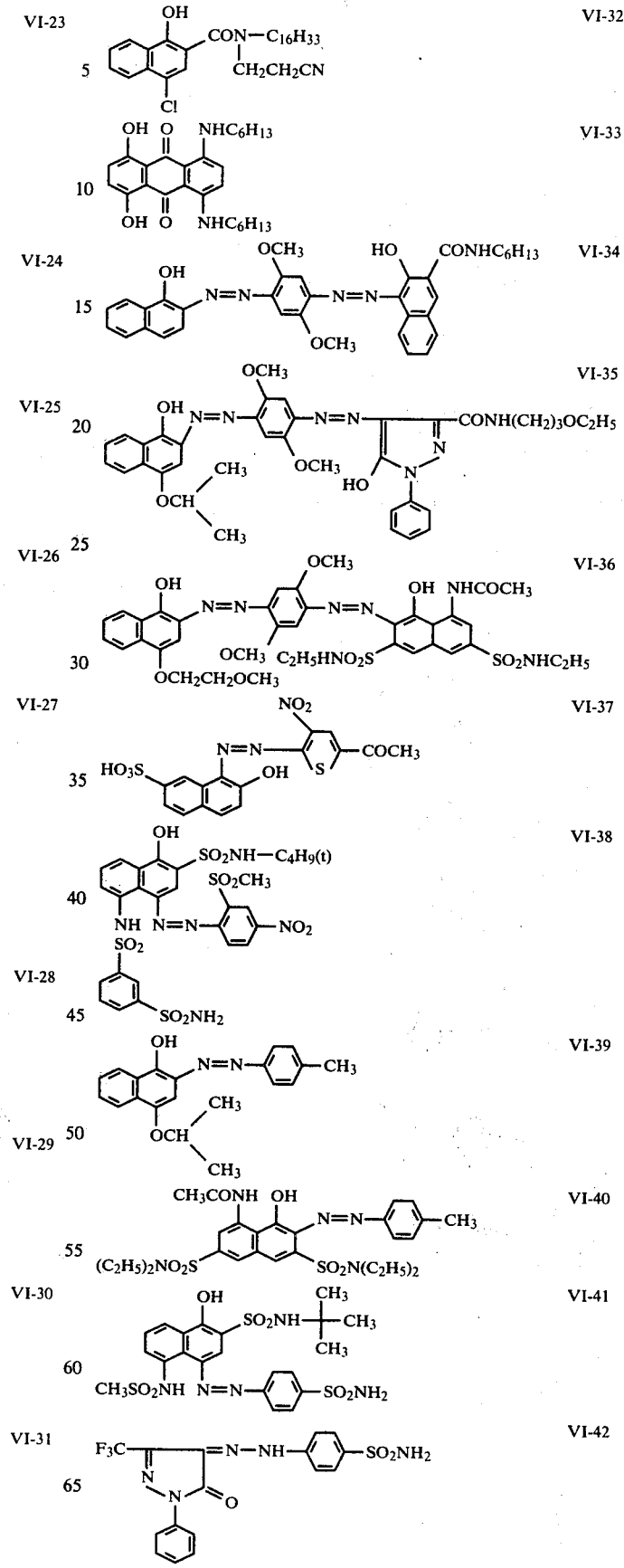

-continued

VI-43
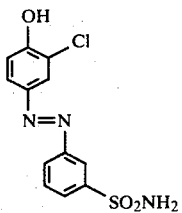

VI-44
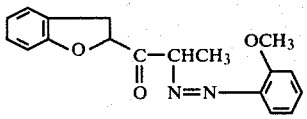

VI-45
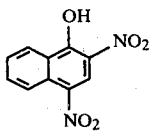

VI-46
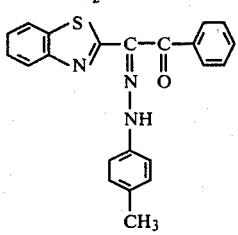

VI-47
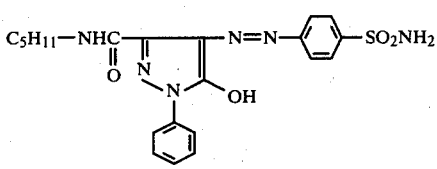

VI-48
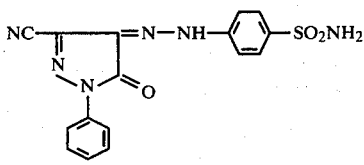

VI-49
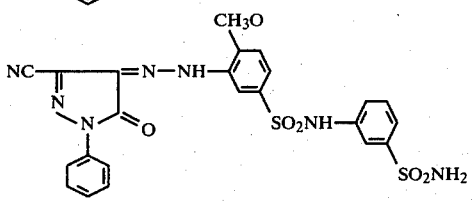

VI-50
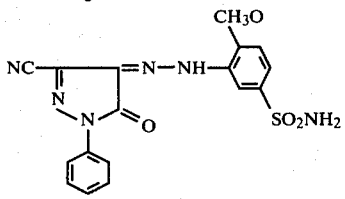

Other types of dyes preferably used in this invention are the dyes formed by the oxidation of DRR compounds such as described in U.S. Published Application B Ser. No. 351,673, U.S. Pat. Nos. 3,932,381, 3,928,312, 3,931,144, 3,954,476, 3,929,760, 3,942,987, 3,932,380, 4,013,635, and 4,013,633, Japanese Patent Application (OPI) Nos. 113,624/76, 109,928/76, 104,343/76 and 4819/77, Japanese Patent Application No. 64,533/77 (published as Japanese Patent Application (OPI) 149,328/1978) and Research Disclosure, 86–74 (1976, Nov.) and Research Disclosure No. 13,024 (1975).

Dyes released by the reaction of an oxidized color developing agent and the DDR couplers also used in this invention are described in British Pat. Nos. 840,731, 904,364, 932,272, 1,014,725, 1,038,331, 1,066,352 and 1,097,064, Japanese Patent Application (OPI) No. 133,021/76, U.S. (U.S. Defensive Publication) T900,029, and U.S. Pat. No. 3,227,550. Still other types of dyes suitably used in this invention are the dye developing agents such as described in Japanese Patent Publication Nos. 182/57, 18,332/57, 32,130/73, 43,950/71 and 2618/74.

Dyes formed by a silver dye bleach process are also suitable. As yellow dyes used for the purpose, there are azo dyes such as Direct Fast Yellow GC (C.I. 29,000), Chrysophenine (C.I. 24,895), etc.; benzoquinone dyes such as Indigo Golden Yellow IGK (C.I. 59,101), Indigosol Yellow 2GB (C.I. 61.726), Algosol Yellow GCA-CF (C.I. 67,301), Indanthrene Yellow GF (C.I. 68,420), Mikethrene Yellow GC (C.I. 67,300), Indanthrene Yellow GK (C.I. 68,405), etc.; anthraquinone series soluble vat dyes; polycyclic soluble vat dyes; and other vat dyes. As magenta dyes used for the above-mentioned purpose, there are illustrated azo dyes such as Sumilight Supra Rubinol B (C.I. 29,225), Benzo Brilliant Geranine B (C.I. 15,080), etc.; indigoid dyes such as Indigosol Brilliant Pink IR (C.I. 73,361), Indigosol Violet 15R (C.I. 59,321), Indigosol Red Violet IRRL (C.I. 59,316), Indanthrene Red Violet RRK (C.I. 67,895), Mikethrene Brilliant Violet BBK (C.I. 6335), etc.; benzoquinone series soluble vat dyes; anthraquinone series soluble vat dyes; heterocyclic soluble vat dyes; and other vat dyes. As cyan dyes used for the above purpose, there are illustrated azo dyes such as Direct Sky Blue 6B (C.I. 24,410), Direct Brilliant Blue 2B (C.I. 22,610), Sumilight Supra Blue G (C.I. 34,200), etc.; phthalocyanine dyes such as Sumilight Supra Turkish Blue G (C.I. 74,180), Mikethrene Brilliant Blue 4G (C.I. 47,140), etc.; Indanthrene Turkish Blue 5G (C.I. 69,845), Indanthrene Blue GCD (C.I. 73,066), Indigosol 04G (C.I. 73,046), Anthrasol Green (C.I. 59,826), etc.

While the mechanism whereby the complex of the present invention improves light fastness is not entirely clear, it is believed that upon exposure to light the organic substrate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention effectively improves the light fastness of the organic substrate.

As described above, the metal complexes are used in this invention for stabilizing the organic substrate materials. These compounds may be incorporated in one or more silver halide emulsion layers of a color photographic material. Also, these compounds may be incorporated in a layer included in the non-sensitive portion of color photographic transfer materials. The complexes can be supplied for stabilizing photographic images by incorporation into the hydrophilic colloids constituting the photographic layers of a photographic element. The complexes are incorporated as a solution thereof in an organic solvent having low boiling point or an organic solvent miscible with water which does not adversely influence the photographic properties of the photographic layers, such as, for example, an alcohol (e.g., methanol, ethanol, isopropanol, butanol, etc.), an ether (e.g., dimethyl ether, ethyl methyl ether, diethyl ether, 1-ethoxypropane, etc.), a glycol (e.g., 1,2-ethanediol, 1,2-propanediol, 1,3-propanediol, etc.), a ketone (e.g., acetone, ethyl methyl ketone, 3-pentanone, etc.), an ester (e.g., ethyl formate, methyl acetate, ethyl acetate, etc.), an amide (e.g., formamide, acetamide, succinamide, etc.), and the like. It is desirable that the complex be incorporated before coating, such as when producing silver halide photographic emulsions, when forming an emulsified dispersion of couplers, or when preparing photographic coating compositions.

In order to introduce these complexes into hydrophilic colloids constituting photographic layers, methods usually employed for dispersing couplers in the color photographic fields may be employed. In this regard, U.S. Pat. Nos. 2,304,939 and 2,322,027 disclose the use of high boiling organic solvents for dissolving these materials. Other applicable methods are described in U.S. Pat. Nos. 2,801,170, 2,801,171 and 2,949,360, wherein low boiling or water-soluble organic solvents are used together with high boiling organic solvents.

Examples of the high boiling organic solvents which are effective for dispersing the substrate material and metal complexes in this invention are di-n-butyl phthalate, benzyl phthalate, triphenyl phosphate, tri-o-cresyl phosphate, diphenylmono-p-butylphenyl phosphate, monophenyl-di-p-tert-butylphenyl phosphate, diphenyl-mono-o-chlorophenyl phosphate, monophenyl-di-o-chlorophenyl phosphate, 2,4-di-n-amylphenol, 2,4-di-t-amylphenol, N,N-diethyllaurylamide as well as trioctyl phosphate and trihexyl phosphate described in U.S. Pat. No. 3,676,137.

The low boiling or water-soluble organic solvents which can be advantageously used together with these high boiling organic solvents are disclosed in, for example, U.S. Pat. Nos. 2,801,171, 2,801,170 and 2,949,360. These organic solvents include:

(1) low boiling organic solvents substantially immiscible in water, such as, for example, methyl acetate, ethyl acetate, propyl acetate, butyl acetate, isopropyl acetate, ethyl propionate, sec-butyl alcohol, ethyl formate, nitromethane, nitroethane, carbon tetrachloride, chloroform, etc. and (2) water-miscible organic solvents such as, for example, methyl isobutyl ketone, $\beta$-ethoxyethyl acetate, $\beta$-butoxytetrahydrofurfuryl adipate, diethylene glycol monoacetate, methoxytriglycol acetate, acetonylacetone, diacetone alcohol, ethylene glycol, acetone, methanol, ethanol, acetonitrile, dimethylformamide, dioxane, etc.

In general, the complex of the formula (I) is dissolved or suspended in an appropriate solvent which is chosen depending upon the physical properties of the complex used from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc., together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamdies, paraffin and mineral waxes as described in U.S. Pat. No. 3,966,468.

In the case of a photographic material, the substrate material (the dye image) and the complex each may be present in one or more of the hydrophilic colloid layers making up a photographic element (e.g., film, paper, diffusion transfer unit, etc.). It is preferred that the metal chelate complex and the organic substrate material be present (i.e., co-exist) in the same emulsion layer, of course, the effects of the present invention can also be attained when the complex and substrate are present in contiguous layers and diffusion occurs between the layers. Were any (further) undesirable diffusion to occur, conventional mordanting techniques could be applied to the present invention.

In the case of incorporating the complex into a silver halide emulsion layer, the complex can be incorporated into each emulsion layer making up the photographic element. In this case, the total amount of complex present is in the range set forth below. The complex and substrate may be present in non-light sensitive elements or layers as well, such as the dye image-receiving layer used in diffusion transfer film units. In the case of image transfer units, the metal chelate complex is preferably located in the layer in which the dye images are finally found, i.e., in an image-receiving layer. Usually, the dye images formed in the image-receiving layer do not diffuse further into any other layer(s) so that the complex is easily maintained in the vicinity of the dye. When the organic substrate material and the complex are incorporated in such a non-photosensitive image-recording or image-receiving element, they are mordanted. The complex contains a ligand capable of retaining it in the mordant layer of the image-receiving element so that it does not diffuse away from the dye stabilized thereby.

A number of types of image transfer film units are particularly appropriate for the practice of the present invention. One is the imhibition transfer film unit set forth in U.S. Pat. No. 2,882,156. The present invention can be further used in conjunction with the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Patents 757,959 and 757,960.

The organic substrate materials and the complexes at the practice of this invention can be used together with the materials as described in *Product Licensing Index*, Vol. 92, No. 9232, 107–110 (1971, December) according to the manner as described therein.

Any amount of the complex will bring about some improvement in the light fastness of the organic substrate and theoretically there is no upper limit for the amount of the complex. Preferably, the complex is present in an amount of at least 0.1 mol% based on 1 mol of the organic substrate material, more preferably in an amount of 0.1 to 1,000 mol%, and most preferably in an amount of 1 to 300 mol%. In the case of a photographic material, the amount is often expressed in terms of a weight unit per square meter of photographic material which can be calculated from the parameters set out above. In the case of a photographic material, the complex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology. As is well known to those skilled in the art, the substrate material is preferably present in the range of from about 10 to $10^4$ micromoles per square meter of the photographic material. A more preferable range is from about 100 to about $3 \times 10^3$ micromoles per square meter of the photographic product.

The organic substrate material used in this invention generally has a maximum absorption peak in the wavelength region less than about 800 nm. However, the organic substrate material having the maximum absorption peak in the region of from about 300 nm to about 800 nm is preferred and the organic substrate material having the maximum absorption peak in the range of from about 400 nm to about 800 nm is most preferred.

In photographic materials based on this invention, any material ordinarily used as the supports for photographic materials may be used as the support therefor in this invention. Examples thereof are cellulose nitrate films, cellulose acetate films, cellulose acetate butyrate films, cellulose acetate propionate films, polystyrene films, polyethylene terephthalate films, polycarbonate films, laminated sheets of these films, and papers. Also, baryta-coated papers, papers coated with α-olefin polymer in particular, a polymer of an α-olefin having 2 to 10 carbon atoms, such as polyethylene, polypropylene, etc., and plastic films the surface of which have been roughened to improve their adhesion to other polymers as shown in Japanese Patent Publication No. 19,068/72 are preferably used as the supports for photographic materials.

In photographic materials used in the method of this invention, various hydrophilic colloids are used. Examples of the hydrophilic colloids used as the binders for photographic silver halide emulsions and/or other coating compositions for photographic layers are gelatin; colloidal albumin; casein; cellulose derivatives such as carboxymethyl cellulose, hydroxyethyl cellulose, etc.; sugar derivatives such as agar agar, sodium alginate, starch derivatives, etc.; synthetic hydrophilic colloids such as polyvinyl alcohol, poly-N-vinylpyrrolidone, polyacrylic acid copolymers, maleic anhydride copolymers, polyacrylamide, and the derivatives or partially hydrolyzed products thereof. If necessary, a mixture of two or more of these colloids which are compatible with each other may be used.

Among the aforesaid materials, gelatin is most generally used but gelatin may be replaced partially or wholly with a synthetic polymer. Furthermore, so-called gelatin derivatives, that is, gelatin modified by treatment with an amino group, an imino group, hydroxy group, a carboxy group, etc., contained in the gelatin molecule as a functional group with a reagent having a functional group which can react with these groups or graft gelatin having bonded thereto the molecular chain of another polymer may be used in place of gelatin.

The silver halide photographic emulsion layers or other photographic layers of photographic materials used in this invention may further contain synthetic polymers such as, for example, water-dispersed vinyl polymers in the form of a latex, in particular, a compound or compounds capable of increasing the dimensional stability of the photographic materials solely or together with a hydrophilic water-permeable colloid.

The silver halide photographic emulsion used in the method of this invention is usually prepared by mixing an aqueous solution of a water-soluble silver salt (e.g., silver nitrate) and an aqueous solution of a water-soluble halogen salt (e.g., potassium bromide) in the presence of a water-soluble polymer solution such as an aqueous solution of gelatin. As such a silver halide, there is silver chloride, silver bromide as well as mixed silver halides such as silver chlorobromide, silver chloroiodide, silver chloroiodobromide, etc. These halide grains may be prepared according to known or conventional processes. As a matter of course, they may be advantageously prepared using the so-called single jet method or double jet method or the controlled double jet method. Also, two or more different silver halide emulsions prepared separately may be used in mixture.

The above-mentioned silver halide photographic emulsions may further contain various compounds for preventing a reduction in sensitivity and the formation of fog during production, preservation or processing of the photographic material. As examples of such compounds, there are 4-hydroxy-6-methyl-1,3,3a,7-tetrazaindene, 3-methylbenzothiazole, 1-phenyl-5-mercaptotetrazole as well as many heterocyclic compounds, mercury-containing compounds, mercapto compounds, metal salts, etc.

The silver halide emulsions used in this invention may also be chemically sensitized in a conventional manner. As examples of chemical sensitizers used for the purpose, there are gold compounds such as an aurichlorate, gold trichloride, etc.; salts of noble metals such as platinum, palladium, iridium, and rhodium; sulfur compounds capable of forming silver sulfide by causing reaction with a silver salt, such as sodium thiosulfate, etc.; stannous salts, amines; and other reducing materials.

The silver halide photographic emulsions used in this invention may, if necessary, be subjected to a spectral sensitization or super dye sensitization using cyanine dyes such as cyanine, merocyanine, carbocyanine, etc., solely or as a combination thereof or using a combination of the cyanine dye or dyes and styryl dyes. These dyes are properly selected according to the objects and use of the photographic materials, such as the wavelength region and sensitivity to be sensitized.

The hydrophilic colloid layers of photographic materials used in the method of this invention can be, if necessary, hardened by various cross-linking agents; for example, aldehyde series compounds, active halogen compounds, vinylsulfone compounds, carbodiimide compounds, N-methylol compounds, epoxy compounds, etc.

In applying the method of this invention to color photographic materials, after image exposure, the color photographic material may be processed in a conventional manner to form color images. The main processing steps in such case are color development, bleach, and fix and, if necessary, other steps such as washing and stabilization. In these steps, two or more steps may be performed in one step as blix step. The color development is usually performed in an alkaline solution containing an aromatic primary amino developing agent. Preferred examples of the aromatic primary amino developing agent are the compounds shown by formulae (A) to (L) described above.

In applying the method of this invention to color photographic materials, wherein the color photographic material is a color photographic diffusion transfer film unit, the processing of the photographic material is carried out automatically in the photographic material. In this case, a color developer containing a color developing agent is contained in a rupturable container. As the developing agent, N-methylaminophenyl, 1-phenyl-3-pyrazolidone, 1-phenyl-4,4-dimethyl-3-pyrazolidone, 1-phenyl-4-methylhydroxymethyl-3-pyrazolidone, 3-methoxy-N,N-diethyl-p-phenylenediamine, etc., in addition to the compounds shown by formulae (A) to (L) above are suitable.

For forming color images in photographic materials based on this invention, various known methods can be used, such as the coupling reaction of the above-described dye-forming color couplers and the oxidation product of a p-phenylenediamine series color developing agent; development with a dye developers; the oxidation cleavage reaction of DRR compounds; the dye-releasing reaction upon coupling of DDR couplers; the dye-forming reaction upon coupling reaction of DDR couplers and a silver dye bleaching process.

Accordingly, this invention can be applied to various kinds of color photographic materials such as color positive films, color papers, color negative films, color reversal films, color diffusion transfer film units, silver dye bleaching photographic materials, etc.

The following examples are provided for further understanding of the method of this invention. They are not to be construed as limiting.

EXAMPLE 1

A solution prepared by dissolving 0.1 g of 1-(2,4,6-trichlorophenyl)-3-(2-chloro-5-tetradecaneamido)anilino-4-{4-(N-ethyl-N-β-methanesulfonamidoethyl)aminophenylimino}-5-oxo-2-pyrazoline in a mixture of 3 ml tricresyl phosphate and 5 ml ethyl acetate was emulsified with 10 g of a 10% gelatin solution containing 1 ml of 1% sodium dodecylbenzenesulfonate aqueous solution. Then the emulsified dispersion thus prepared was blended with 10 g of a 10% gelatin solution, and the mixture was spread over a paper support laminated with polyethylene films on both surface and dried to give Sample A.

Three more samples were prepared by repeating the same procedures described above using the same dispersion but with the use of 28 mg (16.8 mg/m$^2$) of Compound (I-1) characterizing the instant invention for Sample B, and with the addition of 30 (18 mg/m$^2$) and 300 mg (180 mg/m$^2$) of 2,5-ditert-octylhydroquinone, a conventional fade preventing agent for Samples C and D, respectively. The coating rate was 60 mg/m$^2$ calculated as the dye amount. Each of these samples, A to D, was subjected to a 48 hour fading test with a xenon tester (light intensity: 200,000 lux) equipped with a U.V. filter C-40, a product of Fuji Photo Film Co. The result is shown in Table I.

TABLE I

| Sample | Initial Density | Density after Fading Test |
|---|---|---|
| A. | 0.82 | 0.09 |
| B. | 0.83 | 0.62 |

TABLE I-continued

| Sample | Initial Density | Density after Fading Test |
|---|---|---|
| C. | 0.80 | 0.34 |
| D. | 0.82 | 0.43 |

The measurements were carried out using Macbeth Densitometer, type RD-514 equipped with a green filter of status AA grade. It was confirmed that in Sample B containing Compound (I-1) characteristic of the instant invention the density drop was far less than in Samples A, C and D. Particularly, it can be noted that 2,5-di-tert-octylhydroquinone is far less effective than Compound (I-1) of the instant invention even when used in ten-times the amount on a molar basis. Needless to say, Sample C containing the same molar amount as that of Compound (I-1) in Sample B showed insufficient fade preventing effect. This fact demonstrates a surprisingly effective function of this compound on the prevention of light-initiated fading of a dye.

EXAMPLE 2

0.1 g of Compound (VI-2) was dissolved with 0.2 ml 1 N-NaOH and 2 ml methanol. The resulting solution was introduced into 10 g of a 10% gelatin solution. The mixture was coated on a paper support laminated with polyethylene on both surfaces in such a manner that the coating rate of Compound (VI-2) was 80 mg/m$^2$. This product was labeled Sample E. Another sample embodying the instant invention, designated Sample F, was prepared by coating a mixture comprising the same dispersion as used for Sample E having added thereto, immediately before coating, a 2 ml methanol solution containing 44 mg Compound (I-10) of the instant invention (35.2 mg/m$^2$). A comparative Sample G was prepared using 2,4-di-tert-octylhydroquinone a conventional fade preventing agent in an amount of 40 mg (32 mg/m$^2$). In a similar manner as in Example 1, each of these samples was subjected to a 12 hour fading test with the use of the same UV cut filter. The results are summarized in Table II.

TABLE II

| Sample | Initial Density | Density after Fading Test |
|---|---|---|
| E | 0.92 | 0.37 |
| F | 0.90 | 0.76 |
| G | 0.93 | 0.58 |

The measurements were conducted using the same Macbeth Densitometer as in Example 1. The result shows the remarkable fade retarding effect of Compound (I-10) characterizing the instant invention.

EXAMPLE 3

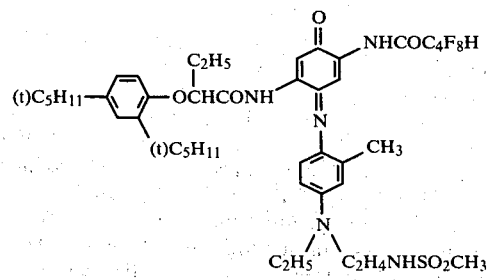

0.1 g of the dye represented by the above structural formula was dissolved in a mixture comprising 3 ml dibutyl phthalate and 5 ml ethyl acetate. The resulting solution was emulsified in 10 g of a 10% aqueous gelatin solution containing 1 ml of a 1% sodium dodecylbenzenesulfonate. After blending with 10 g of the 10% gelatin solution, this dispersion was coated on a paper support laminated on its both surfaces with polyethylene film and dried. The sample was designated H.

Similar procedures were repeated to prepare Sample I with incorporation of Compound (I-11) embodying the instant invention by 36 mg (18 mg/m$^2$) to the same dispersion, and Sample J with the use of 120 mg (60 mg/m$^2$) α-tocopherol which is a conventional fade preventing agent to the same dispersion. The coating conditions for each sample was so adjusted to give a coating rate for the dye of 50 mg/m$^2$. Each sample was subjected to a 48 hour fading test in a xenon tester equipped with a U.V. cut filter (C-40, a product of Fuji Photo Film Co.) at an intensity of 200,000 lux. The result is shown in Table III.

TABLE III

| Sample | Initial Density | Density after Fading Test |
|---|---|---|
| H | 0.85 | 0.25 |
| I | 0.84 | 0.69 |
| J | 0.82 | 0.46 |

A Macbeth Densitometer RD 514 equipped with a red filter of Status AA was employed for the measurement.

From this result, it is evident that Compound (I-11) characterizing the instant invention quite effectively prevents the cyan dye from fading by light. Moreover, the fact that efficient fade retarding agents have not been known for cyan dyes as yet is indicative of the significance of the discovery on which the instant invention is based.

EXAMPLE 4

Into a mixture comprising 30 ml tricresyl phosphate, 5 ml dimethylformamide and 5 ml ethyl acetate was dissolved 10 g of a magenta coupler, 1-(2,4,6-trichlorophenyl)-3-{(2-chloro-5-tetradecaneamido)anilino}-2-pyrazolin-5-one. The solution thus obtained was dispersed in 80 g of a 10% gelatin solution containing 8 ml of a 1% sodium dodecylbenzenesulfonate solution.

A coating mixture was prepared comprising 145 g of a green sensitive silver chlorobromide emulsion (Bromide content=50 mol %) which contained 7 g of Ag, the whole amount of the dispersion made above and an additional amount of sodium dodecylbenzenesulfonate as coating aid, and coated on a paper support laminated with polyethylene on both surfaces. The product was designated Sample K. The coating rate of the coupler was 400 mg/m$^2$.

Sample L embodying the instant invention was prepared with 2.7 g (108 mg/m$^2$) of Compound (I-11) of the instant invention added to the dispersion, which composition was coated in a similar manner. Further, Sample M was produced using 1.0 g (40 mg/m$^2$) of 2,5-di-tert-octylhydroquinone which is a conventional fade preventing agent added to the same composition for Sample K through a similar coating operation. These samples were exposed to 1000 lux light for one second and then processed with processing solution of the following compositions.

| Developer: | |
|---|---|
| Benzyl Alcohol | 15 mg |
| Diethylenetriamine Pentaacetic Acid | 5 g |
| KBr | 0.4 g |
| Na$_2$SO$_3$ | 5 g |
| Na$_2$CO$_3$ | 30 g |
| Hydroxylamine Sulfate | 2 g |
| 4-Amino-3-methyl-N-ethyl-N-β-(metasulfonamido)-ethylaniline . 3/2 H$_2$SO$_4$ . H$_2$O | 4.5 g |
| Water to make | 1000 ml |
| pH = 10.1. | |
| Blix solution: | |
| Ammonium Thiosulfate (70 wt %) | 150 ml |
| Na$_2$SO$_3$ | 5 g |
| Na[Fe(EDTA)] | 40 g |
| EDTA | 4 g |
| Water to make | 1000 ml |
| pH = 6.8 | |

| Processing conditions: | Temperature | Duration |
|---|---|---|
| Development | 33° C. | 3 min 30 sec |
| Blix | 33° C. | 1 min 30 sec |
| Washing | 28–35° C. | 3 min |

Each sample provided with the thus formed dye image was exposed to sunlight for 2 weeks through a U.V. cut filter C-40 (a product of Fuji Photo Film Co.) which eliminates light having wavelengths shorter than 400 nm.

The degree of dye decomposition is shown in Table IV. The density measurement was performed with a Macbath Densitometer RD-514 equipped with Status AA filters by measuring the density after sunlight exposure of an area having an initial density of 2.0.

TABLE IV

| Sample | Density after Sunlight Exposure | Dye Remnant* |
|---|---|---|
| K | 0.96 | 48% |
| L | 1.85 | 93% |
| M | 1.34 | 64% |

*Dye Remnant = (Density after sunlight exposure/2.0 × 100

The result exhibits clearly that Compound (I-11) of the instant invention is an effective fade preventing agent.

While the invention has been described in detail and with reference to specific embodiments thereof, it will be apparent to one skilled in the art that various changes and modifications can be made therein without departing from the spirit and scope thereof.

What is claimed is:

1. An element stabilized against the action of light comprising the combination of
   (a) a photographically useful dye having an absorption maximum in the wavelength range between about 300 nm and about 800 nm, and
   (b) at least one complex compound represented by one of the following general formulae (I) and (II):

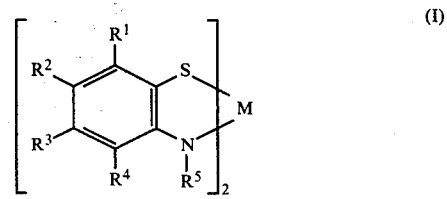

-continued

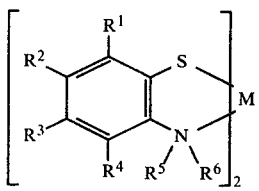
(II)

wherein M is a metal selected from the group consisting of Cu, Co, Ni, Pd and Pt; $R^1$, $R^2$, $R^3$ and $R_4$ each represent a hydrogen atom, a halogen atom, a cyano group, an alkyl group, an aryl group, a cycloalkyl group, or a heterocyclic group attached to the carbon atom of the benzene ring directly or through a divalent connecting group; or, $R^1$ and $R^2$, $R^2$ and $R^3$, or $R^3$ and $R^4$ can be combined to represent non-metallic atoms necessary to complete a 6-membered ring; and $R^5$ and $R^6$, which may be the same or different, each represent a hydrogen atom, an alkyl group, an aryl group, an acyl group, an alkoxycarbonyl group, an aryloxycarbonyl group, an alkylsulfonyl group or an arylsulfonyl group.

2. The element of claim 1, wherein said complex compound is represented by the formulae (Ia) and (IIa)

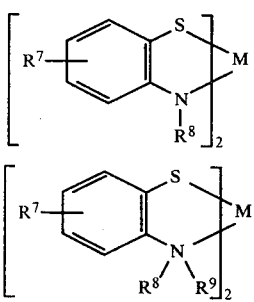
(Ia)

(IIa)

wherein M has the same definition as in formulae (I) and (II), $R^7$ has the same definition as $R^1$-$R^4$ in formulae (I) and (II), and $R^8$ and $R^9$ each have the same definition as $R^5$ and $R^6$ in the formulae (I) and (II).

3. The method of claim 1, wherein said dye is selected from the group consisting of anthraquinone dyes, quinoneimine dyes, azo dyes, methine dyes, polymethine dyes, indoamine dyes, indophenol dyes and formazan dyes.

4. The method of claim 1, wherein said dye is the photographic dye image formed from a dye-forming coupler, a DDR coupler, a DRR compound, a dye developer, or a dye formed in a silver dye bleaching process.

5. The element of claim 4, wherein said dye-forming coupler is a benzoylacetanilide or α-pivalyacetanilide yellow dye-forming coupler, a 5-pyrazolone, indazolone, pyrazolinobenzimidazole, pyrazolo-s-triazole, or cyanoacetylcumarone magenta dye-forming coupler, or a phenol or naphthol cyan dye-forming coupler.

6. A color photographic material comprising at least one layer containing a photographic dye image, said dye of said dye image having an absorption maximum in the wavelength range between about 300 nm and about 800 nm, wherein said layer or an adjacent layer thereto contains at least one complex compound represented by the formula (I) or the formula (II)

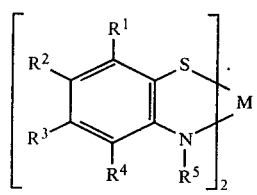
(I)

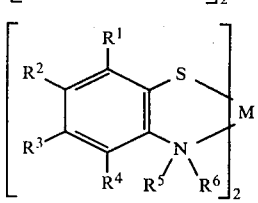
(II)

wherein N is a metal selected from the group consisting of Cu, Co, Ni, Pd and Pt; $R^1$, $R^2$, $R^3$ and $R^4$ each represent a hydrogen atom, a halogen atom, a cyano group, an alkyl group, an aryl group, a cycloalkyl group, or a heterocyclic group attached to the carbon atom of the benzene ring directly or through a divalent connecting group; or, $R^1$ and $R^2$, $R^2$ and $R^3$, or $R^3$ and $R^4$ can be combined to represent non-metallic atoms necessary to complete a 6-membered ring; and $R^5$ and $R^6$, which may be the same or different, each represent a hydrogen atom, an alkyl group, an aryl group, an acyl group, an alkoxycarbonyl group, an aryloxycarbonyl group, an alkylsulfonyl group or an arylsulfonyl group, stabilizing said dye to the action of light.

7. The color photographic material of claim 6, wherein said complex compound is represented by the formula (Ia) and (IIa)

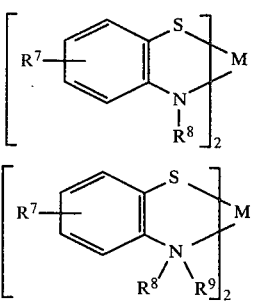
(Ia)

(IIa)

wherein M has the same definition as in formulae (I) and (II), $R^7$ has the same definition as $R^1$ and $R^4$ in formulae (I) and (II), and $R^8$ and $R^9$ each have the same definition as $R^5$ and $R^6$ in the formulae (I) and (II).

8. The color photographic material of claim 6 or 7, wherein said photographic dye image is formed from a color coupler, a DDR coupler, a DRR compound, a dye developer, or a dye formed in a silver dye bleaching process.

9. The color photographic material of claim 8, wherein said dye is formed by the reaction of a primary aromatic amine color developing agent and a cyan, magenta or yellow dye image forming coupler.

10. The photogrphic material of claim 9, wherein said photographic dye image is composed of at least one dye selected from the group consisting of anthraquinone dyes, quinoneimine dyes, azo dyes, methine dyes, polymethine dyes, indoamine dyes, indophenol dyes and formazan dyes.

11. The photographic material of claim 9, wherein said dye image forming coupler is a benzoylacetanilide or α-pivalyacetanilide yellow dye-forming coupler, a 5-pyrazolone, indazolone, pyrazolinobenzimidazole, a pyrazolo-s-triazole, or cyanoacetylcumarone magenta dye-forming coupler, or a phenol or naphthol cyan dye-forming coupler.

12. The element of claim 1, wherein said element is a photographic solution, a photographic layer or layers, or a photographic material.

13. The element of claim 12, wherein said element is a photographic material and wherein said combination of said dye and said at least one complex compound represented by the formulae (I) and (II) is incorporated into at least one layer selected from the group consisting of one of more hydrophilic colloid layers and one or more photographic emulsion layers in said photographic material.

14. The element of claim 13, wherein said complex compound represented by the formulae (I) and (II) and said dye are incorporated into separate layers but layers contiguous thereto or are incorporated as a combination in the same layer.

* * * * *